United States Patent [19]

Pyle

[11] Patent Number: 5,475,449
[45] Date of Patent: Dec. 12, 1995

[54] SAFETY GLASS/EAR PLUG COMBINATION

[76] Inventor: Nigel Pyle, 17693 Huntleigh Ct., Apt. 102, Country Club Hills, Ill. 60478

[21] Appl. No.: 124,662

[22] Filed: Sep. 22, 1993

[51] Int. Cl.⁶ .......................... G02C 11/00; A61F 11/08; A61F 11/12
[52] U.S. Cl. .......................... 351/123; 351/156; 351/157; 351/158; 24/3.3; 181/130
[58] Field of Search ........................... 2/423, 426, 448; 24/3 B, 3 C, 3.3; 181/130, 131, 132, 133, 134, 135; 128/864, 865, 866; 351/111, 121, 122, 123, 155, 156, 157, 158; D24/106

[56] References Cited

U.S. PATENT DOCUMENTS

| | | | |
|---|---|---|---|
| D. 241,881 | 10/1976 | Peterson et al. | D24/106 |
| D. 262,491 | 12/1981 | Ebert | D24/106 |
| 2,798,409 | 7/1957 | Speers | 351/157 |
| 3,000,462 | 9/1961 | Smith | 181/23 |
| 3,807,526 | 4/1974 | Sygnator | 351/123 |
| 3,856,007 | 12/1974 | Leight | 128/152 |
| 3,871,372 | 3/1975 | Bivins | 128/152 |
| 4,174,155 | 11/1979 | Herman | 351/158 |
| 4,314,553 | 2/1982 | Westerdal | 128/152 |
| 4,902,120 | 2/1990 | Weyer | 351/158 |
| 4,965,913 | 10/1990 | Sugarman | 24/3 C |
| 5,074,375 | 12/1991 | Grozil | 181/135 |
| 5,092,667 | 3/1992 | Bagley | 351/156 |
| 5,092,668 | 3/1992 | Welch et al. | 351/156 |
| 5,133,596 | 7/1992 | Korny et al. | 351/158 |

Primary Examiner—William L. Sikes
Assistant Examiner—David R. Parsons
Attorney, Agent, or Firm—JoAnne M. Denison; Michael Best & Friedrich

[57] ABSTRACT

The present invention consists of a device which removeably secures a standard set of earplugs to a pair of eyeglasses, preferably safety glasses, by double looping a standard cord with a pair of cord adjusters. A pair of double looped elastomeric temple securing means hold both a loop of the cord through one of each of their loops and an eyeglass temple piece through the other of their loops. The tips of the cord are provided with an annular binding surface which may be inserted into the end of a standard earplug cavity which is cylindrical in configuration and which secures the earplug to the cord tip by frictional engagement therewith.

14 Claims, 3 Drawing Sheets 5,475,449

SAFETY GLASS/EAR PLUG COMBINATION

BACKGROUND OF THE INVENTION

The present invention relates to the area of ear and eye protection devices which are used in industrial and factory applications. More specifically, it relates to ear and eye protection combinations wherein a pair of earplugs is conveniently attached to a pair of eyeglasses. In many cases the eyeglasses will consist of safety glasses.

In many industrial plants and factories, workers are required to wear safety glasses and/or earplugs in order to protect their eyes from flying objects and their ears from excessive noise levels in the plant. One particularly common and very effective form of earplugs consists of a baffled cone shaped member having a cavity or recess in its back end. The earplugs are attached to each other simply by a shoelace-like cord which has each of its end tips bound with a small ring of a thin transparent vinyl or a cellophane type material to prevent fraying of the cord. This bound surface provides a bearing surface which can be inserted into a cylindrical cavity or recess located in the back end of an earplug by frictional engagement therewith. Such earplug cord assemblies are commonly draped across the user's neck when the earplugs are not in use.

However, many users of these devices also wear glasses and, in many cases, they wear safety glasses. Often a factory worker or machine operator will need to hunt for a pair of safety glasses and then hunt for a pair of earplugs. The present invention eliminates the need to look for both of these items, and it encourages factory works to always wear both safety glasses and earplugs at the same time, thus reducing injuries to both eyes and ears. In many plants, often safety glasses and the earplugs are kept separate from one another so that a factory worker may be tempted to wear one, but not both of these devices. Or, a factory, worker may misplace one, but not both of the devices, and may be tempted to enter the work area without complete protection.

The present invention solves these difficulties by adapting the standard earplug and cord assembly which is presently on the market and in common use so that it can be removeably attached to a pair of eyeglasses. In this way, factory or plant management can separately purchase a pair of elastomeric loops and adjusters and secure them on the cord of a set of standard earplugs and then attach the invention to a standard set of safety glasses. Thus the invention can be dispensed as a unit so that workers will be encouraged to wear both forms of protection at all times.

In an alternative form, standard safety glasses can be purchased which have a hole or aperture through each temple. In this way, a factory worker can simply remove the earplug at the tip of the cord and insert the cord through each aperture. From that point on, whenever the factory worker reaches for a pair of eyeglasses, the earplugs will be removeably attached.

The invention in this form, can secure a standard earplug assembly to a pair of eyeglasses and/or safety glasses for a very nominal cost with simple, inexpensively designed elements.

OBJECTS OF THE INVENTION

Therefore, it is an object of the present invention to provide a device with simple, inexpensive elements which are capable of removably securing a pair of eyeglasses or safety glasses to a standard earplug cord assembly.

It is another object of the present invention to provide a device wherein a cord can be used to secure earplugs to either of its ends, and at the same time pass through an aperture located in each temple piece of a pair of eyeglasses so that a standard set of earplugs with a cord can be used to secure the earplug cord assembly to a set of eyeglasses.

It is yet a further object of the present invention to provide an earplug assembly wherein stoppers are provided along the cord so that the earplugs are always in convenient reach for the operator to insert in his or her ears.

These and other objects will be readily apparent from the description of the preferred embodiments which follow herein.

DETAILED DESCRIPTION OF THE DRAWINGS

Figure 1:
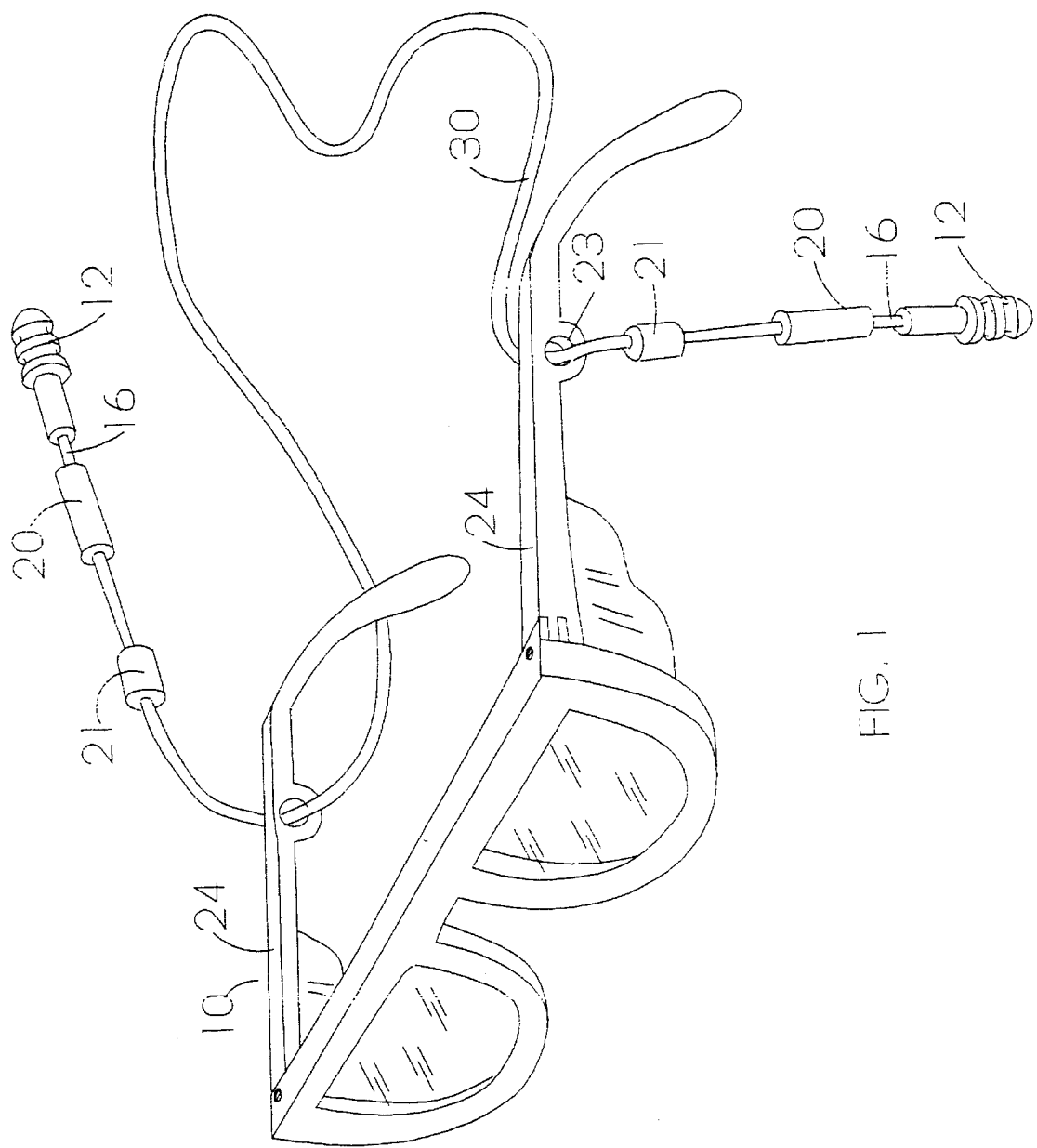
FIG. 1 shows a perspective view of a first embodiment of the present invention.

Referring now to FIG. 1, is shown a pair of eyeglasses or safety glasses 10 as they are attached to the first embodiment of the present invention, earplug and cord assembly 30. Cord 11 is constructed from a simple flexible connector which may be made from stock cord, shoe laces, or any flexible vinyl, rubber or polymeric material. Cord 11 is provided with a standard earplug 12 which consists of baffled cone shaped member 13 and earplug back member 14. The earplug back member 14 has a cylindrical cavity 15 or recess which is capable of receiving a standard tip of a shoe lace or cord which has been bound to prevent fraying. FIG. 1 also shows cord end cover members 20 which snugly fit over cord 11, and when pushed up against earplug 12 they provide an elongated surface so that the user may easily insert and remove earplugs 12. FIG. 1 also shows cord stoppers 21 which are located at a distance of approximately 2 to 3 inches from each end of cord 11. The cord stoppers 21 are movably secured by frictional engagement with cord 11 so that the user may determine the best length from each earplug 12 to temple piece 24 and in between cord stoppers 21 which is comfortable for him or her. A distance of 2 inches as the distance between earplugs 12 and temple pieces 24 is recommended for easiest insertion and removal of earplugs 12 by the user of this device. A distance of approximately 33 inches between cord stoppers 21 is recommended as the most convenient length to allow the device to hang comfortably from the user's neck when it is removed.

Figure 4:
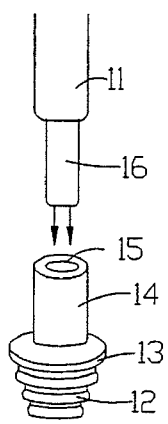
FIG. 4 shows a perspective view of a detail of a standard cord tip which has been inserted into a standard earplug.

Turning now to FIG. 4 is shown the detail of each end of cord 11. The end of the cord 11 is provided with a binding element 16 which consists of a thin flexible sheet of transparent vinyl, polymeric material or cellophane which is wrapped around the end of the cord to prevent it from fraying. It is this surface of binding element 16 which is capable of bearing upon the interior of cylindrical cavity 15 so as to fictionally secure the end of the cord 11 to the earplug 12. Although a cylindrical configuration of the tip of cord 11 is shown with a corresponding cylindrical cavity 15, it is anticipated that any other shape or configuration may be used, such as oval, square or rectangular.

Figure 2:
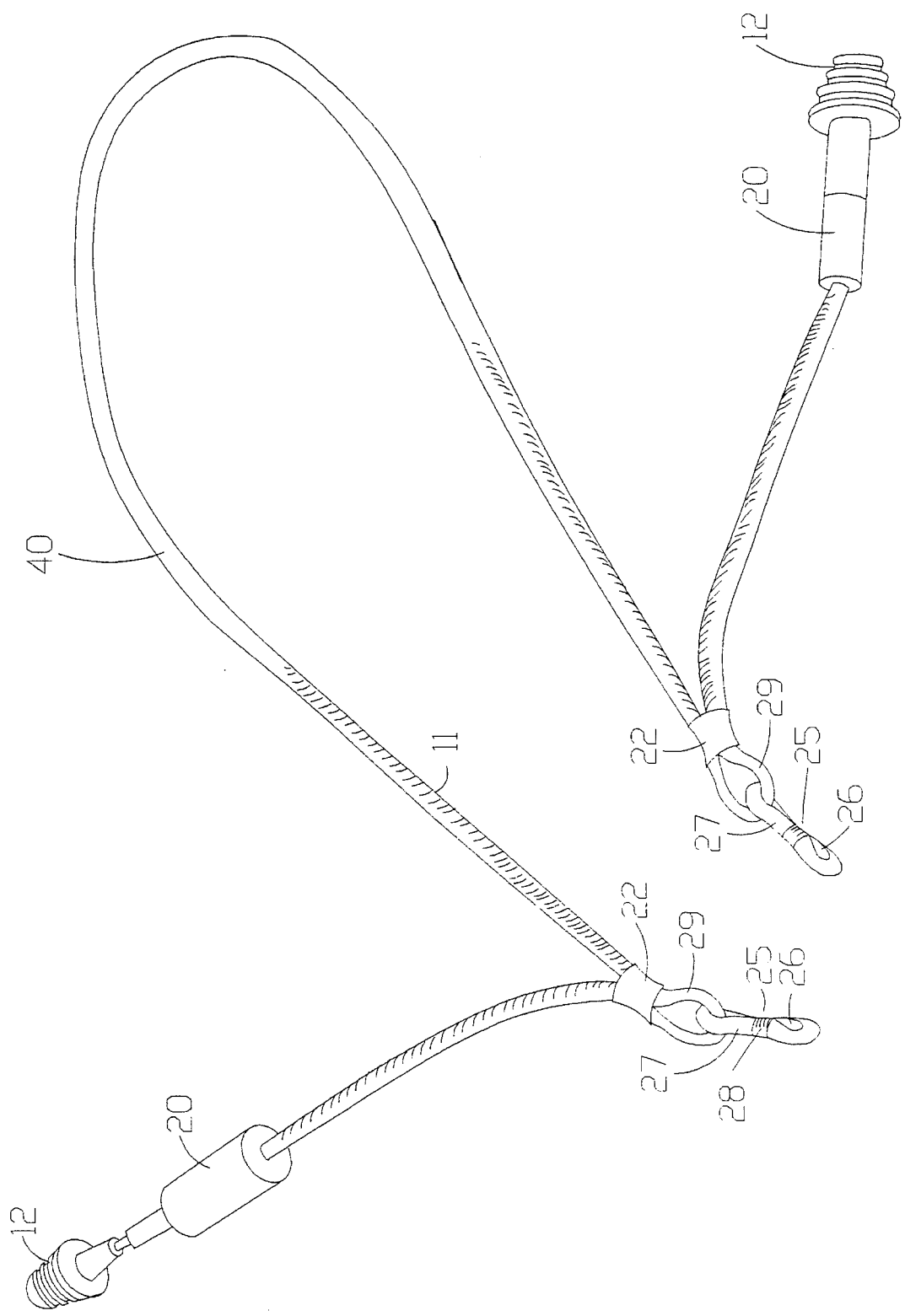
FIG. 2 shows a perspective view of a second embodiment of the present invention.

Turning now to FIG. 2 is shown a second embodiment of the present invention, eyeglass attachment assembly 40. In the second preferred embodiment is shown cord 11 which is looped at approximately 2 to 3 inches from either end with a pair of encircling cord adjusters 22 which are made out of a flexible vinyl, rubber or rubber based polymer. The cord adjusters 22 are sufficiently tight so as to retain two diameters of cord 11 against movement by frictional engagement therewith. Again, a distance of 33 inches is recommended between cord adjusters 22 so that the device will hang comfortably around the user's neck when it is removed.

The end loop 29 which is created when the cord adjusters 22 are attached to cord 11 holds temple securing means 25. Temple securing means 25 consists of a pair of loops on either end wherein the first loop is a cord securing loop 27 and other loop is a temple securing loop 26. Temple securing loop 26 and cord securing loop 27 are preferably made from elastomeric material such as a flexible vinyl or rubber or rubber based polymer. Loop clamp 28 permanently binds the two loops, temple securing loop 26 and cord securing loop 27, together in the central portion between them by bearing against these two loops. Loop clamp 28 therefore may be made from metal or any other rigid tough polymeric substance that can tightly retain and bind together two cord-like elements. It is necessary for temple securing loop 26 to be made from an elastomeric material so that temple piece 24 can pass there through and the temple securing means 25 can be held in place by the frictional engagement of temple securing loop 26 against temple piece 24.

FIG. 2 also shows cord end cover member 20 which is provided with a standard earplug assembly and provides an elongated surface for the user to grab and insert or remove the earplug. In FIG. 1, cord cover member 20 is shown in its retracted position so that the end of the cord containing binding element 16 can be secured to the earplug by means of cylindrical cavity member 15 present in earplug back member 14. After the earplug 12 has been secured to earplug back member 14, the cord end cover member 20 is slid into position to bear against earplug back member to provide an elongated surface for easy insertion and removal of earplug 12. This position is shown in FIG. 2.

Of course, eyeglass attachment assembly 40 can either be sold in its present form or it can be created by the user with a standard earplug and cord set. The user would simply thread cord 11 through a cord adjuster 22, place cord securing loop 27 through cord 11, thread cord 11 back through the same cord adjuster 22, place cord end cover member 20 over cord 11 and then place the earplug 12 on the end of cord 11. The user could adjust cord adjuster 22 so that the earplug 12 will hang at preferably 2 inches from the eyeglass temple pieces 24 when the assembly process is complete. A distance of 2 inches is recommended because the user can easily locate and insert earplugs 12 in one easy motion. The eyeglass attachment assembly 40 could then be slipped on to temple pieces 24 of a pair of eyeglasses.

Figure 3:
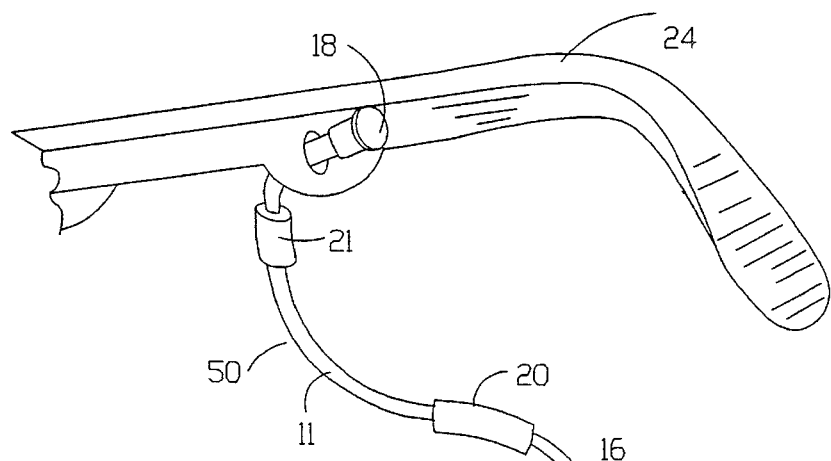
FIG. 3 shows a perspective view of one temple piece of eyeglasses utilizing yet a third embodiment of the present invention.

Turning now to FIG. 3 is shown a third embodiment of the present invention where two separate earplug cord assemblies 50 are attached to a pair of eyeglass temple pieces 24. In this instance, end cap 18 is placed over binding element 16 to secure each eyeglass assembly attachment 50 to temple 24.

Figure 5:
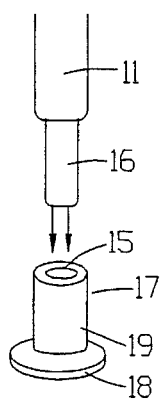
FIG. 5 shows a perspective view of a detail of a standard cord tip which has been inserted into an end cap.

FIG. 5 shows the detail of the end of cord 11 in the vicinity of binding element 16. Binding element 16 is slipped into cylindrical cavity 15 and is held in place by frictional engagement therewith. End cap 17 consists of flange 18 which provides a gripping surface for the user, and cylindrical back member 19. At the back end of cylindrical member 19 is cylindrical cavity 15 which is adapted to receive the binding element 16 of cord 11. In this manner, two earplug cord assemblies 50 can be attached to two temples 24 of a pair of eyeglasses. Like the other embodiments of the present invention which appear in FIGS. 2 and 1, eyeglass attachment assembly 50 consists of cord 11 with cord end cover member 20 being slideably received upon cord 11 which, when in use, provides an elongated surface which the user can grab for easy insertion and removal of the earplug. Again, it is recommended that the length of cord 11 from end cap 17 to earplug 12 be approximately two to three inches, with two inches being preferred so that the user of this device can easily insert and remove earplugs 12.

Although in the foregoing description the present invention has been described by reference to several specific body embodiments, it is to be understood that modifications and alterations in the structure and arrangement of the invention other than those set forth herein may be achieved by those skilled in the art and that such modifications and alterations are to be considered as within the scope of this invention.

What is claimed is:

1. A device for securing a pair of ear plugs to a pair of eyeglasses having;

elongated flexible connecting means having two ends;

a pair of ear plugs secured to both ends of the elongated flexible connecting means;

a pair of eyeglass temple pieces:

a pair of apertures with one aperture located in each temple piece of the pair of eyeglasses where each aperture is adapted to receive the end of each elongated flexible connecting means which passes therethrough;

a pair of stoppers frictionally placed along the length of the elongated flexible connecting means and bearing thereupon so as to maintain the earplugs in proper position so that the user may comfortably remove and insert the earplugs.

2. The device according to claim 1 wherein the elongated flexible connecting means comprises a cord.

3. The device according to claim 2 wherein the cord further has;

a pair of binding elements encircling either end of the cord to prevent the cord from unravelling and to provide a bearing surface for securing the ear plugs to the cord.

4. The device according to claim 3 wherein the ear plugs each have a cylindrical aperture adapted to receive each of the binding elements encircling either end of the cord for securing the earplug to the binding elements by frictional engagement therewith.

5. A device for securing a pair of earplugs to a pair of eyeglasses having;

elongated flexible connecting means having two ends;

a pair of ear plugs secured to either end of the elongated flexible connecting means;

a pair of cord adjusters frictionally placed along the length of the elongated flexible connecting means so as to maintain the earplugs in proper position along the length of the elongated flexible connecting means;

a pair of elastomeric temple securing means;

wherein each cord adjuster holds a loop of the elongated flexible connecting means in frictional engagement therewith and the loop further secures the device to the pair of eyeglasses by passing each eyeglass temple through each loop of the elongated flexible connecting means.

6. The device according to claim 5 wherein the pair of elastomeric temple securing means each have;

two loops of flexible elastomeric material, one of which allows the elongated flexible connecting means to pass therethrough, and the other of which allows one of the eyeglass temple pieces to pass therethrough and frictionally secure the loop to the eyeglass temple pieces.

7. The device according to claim 5 wherein the elongated flexible connecting means comprises a cord.

8. The device according to claim 7 wherein the cord further has;

a pair of binding elements encircling either end of the cord to prevent the cord from unravelling and to provide a bearing surface for securing the ear plugs to the cord.

9. The device according to claim 8 wherein the ear plugs each have an annular aperture adapted to frictionally engage each of the binding elements encircling either end of the cord and secure it thereto.

10. A device for securing a pair of ear plugs to a pair of glasses having;

a pair of elongated flexible connecting means;

a pair of earplugs secured to one end of each of the elongated flexible connecting means;

a pair of eyeglass temple pieces;

a pair of apertures with each aperture located in each temple piece of the pair of eyeglass where each aperture is adapted to receive at least one end of the elongated flexible connecting means;

securement means at one end of each of the elongated flexible connecting means to secure each elongated flexible connecting means to each pair of eyeglass temple pieces after each elongated flexible connecting means has been passed through each aperture located in each temple piece so as to maintain the earplugs in proper position so that the user may comfortably remove and insert the earplugs.

11. The device according to claim 10 wherein each of the elongated flexible connecting means comprises a cord.

12. The device according to claim 11 wherein each of the cords further has;

a binding element encircling one end of the cord to prevent the cord from unravelling and to provide a bearing surface for securing an ear plug to the cord.

13. The device according to claim 12 wherein each ear plug has a cylindrical aperture adapted to frictionally engage a binding element encircling one end of the cord and secure the earplug thereto.

14. The device according to claim 12 wherein each of the cords further has;

an end cap with a cylindrical cavity adapted to frictionally engage one end of the cord to secure the cord to an eyeglass temple pieces.

* * * * *